(12) United States Patent
Shong et al.

(10) Patent No.: US 8,405,719 B2
(45) Date of Patent: Mar. 26, 2013

(54) APPARATUS AND METHOD FOR MEASUREMENT OF CORONA DISCHARGE OF POWER FACILITIES BY UV SENSOR WITH OPTIC LENS

(75) Inventors: Kil Mok Shong, Kangwon-Do (KR); Young Seok Kim, Gyeonggi-Do (KR)

(73) Assignee: Korea Electric Safety Corp., Seoul (KR)

( * ) Notice: Subject to any disclaimer, the term of this patent is extended or adjusted under 35 U.S.C. 154(b) by 346 days.

(21) Appl. No.: 12/806,578

(22) Filed: Aug. 17, 2010

(65) Prior Publication Data
US 2011/0273560 A1  Nov. 10, 2011

(30) Foreign Application Priority Data
May 4, 2010  (KR) .................. 10-2010-0041983

(51) Int. Cl.
*H04N 7/18*  (2006.01)
(52) U.S. Cl. .................. 348/135; 250/330; 250/372
(58) Field of Classification Search .............. 250/330, 250/372; 348/135
See application file for complete search history.

(56) References Cited

U.S. PATENT DOCUMENTS

| 6,323,491 B1 * | 11/2001 | Forsyth ................. 250/372 |
| 2006/0043296 A1 * | 3/2006 | Mian et al. ............. 250/330 |

FOREIGN PATENT DOCUMENTS

WO  WO 00/05536  *  2/2000

OTHER PUBLICATIONS

Ofil Systems, Ofil's bispectral imaging technology, Apr. 13, 2009, <http://web.archive.org/web/20090413144258/http://www.ofilsystems.com/UVtech/bispectral.html>.*

* cited by examiner

*Primary Examiner* — Mehrdad Dastouri
*Assistant Examiner* — Joseph Sanford
(74) *Attorney, Agent, or Firm* — Harness, Dickey & Pierce, P.L.C.

(57) ABSTRACT

The present disclosure relates to a method and apparatus for measuring corona discharge of power facilities by a UV sensor with an optical lens. The apparatus includes a UV sensor array receiving UV rays from an analyzing target of a power facility at a location separated a predetermined distance from the target, an optical lens unit focusing the UV rays to the UV sensor array, a signal detector detecting the UV rays in the form of a pulse voltage waveform signal, a UV image processor processing the detected pulse voltage waveform signal into a UV image, a real image measurement unit photographing a real image of the analyzing target, a real image processor displaying a photographed real image; a matching unit combining the photographed real image with the UV image, and an image/data output unit detecting a location of corona discharge based on the combined UV image and real image.

2 Claims, 8 Drawing Sheets

APPARATUS AND METHOD FOR MEASUREMENT OF CORONA DISCHARGE OF POWER FACILITIES BY UV SENSOR WITH OPTIC LENS

CROSS-REFERENCE TO RELATED APPLICATIONS

This application claims the benefit and priority of KR 10-2010-0041983, filed May 4, 2010. The entire disclosure of the above application is incorporated herein by reference.

BACKGROUND OF THE INVENTION

1. Field of the Invention

The present invention relates to a method and apparatus for measuring corona discharge of power facilities by a UV sensor with an optical lens and, more particularly, to a method and apparatus for measuring corona discharge of power facilities that may effectively analyze conditions of power facilities by accurately detecting a location of corona discharge through a UV sensor with an optical lens and matching a real image with a UV image to detect a location generating UV rays upon corona discharge caused by degradation or insulation deterioration of the power facilities.

2. Description of the Related Art

Power facilities refer to an aggregate of instruments for use in controlling transfer, storage, transformation, and shielding of electric energy. The power facilities generally undergo insulation failure under negative conditions, such as long-term use at high voltage, manufacturing defect, installation defect, and the like.

Particularly, current flow on surfaces or discharge in air can lead to various accidents such as electric power interruption, fire, damage to power facilities, and the like under negligence of security management.

In general, when a defect is formed on a certain component used in large size electric power facilities including power cables and other components, partial discharge occurs from this defect and continuation of the partial discharge results in discharge by insulation deterioration on the surfaces of the power facilities or in air, which leads to insulation failure of the power cables and other components.

Although there are various direct factors causing insulation deterioration of insulators, such as temperature, humidity, mechanical vibration, and other conditions around the insulators, the most representative direct factor of insulation deterioration is internal partial discharge.

Phenomena caused by the partial discharge include light emission, noise, electric energy emission, gas discharge, and the like.

If discharge by insulation deterioration on the surfaces of the power facilities or discharge in air can be measured at an initial time, the power cables and other components of the power facilities can be prevented from undergoing insulation failure.

FIG. 1 is a schematic cross-sectional view of a conventional UV sensor. When UV rays are emitted due to corona discharge resulting from insulation deterioration, photons are discharged and detected by an anode and cathode of a photo receiver in the UV sensor A conventional apparatus for detecting insulation deterioration based on corona discharge is a measurement system that includes an array of such UV sensors and a main system for receiving and analyzing signals.

Among such conventional systems, a system for detecting insulation deterioration using an ultrasound sensor can detect insulation deterioration only after the deterioration proceeds to some degree, and thus cannot detect an initial state of insulation deterioration, thereby providing a high frequency of erroneous detection.

Therefore, recently, a discharge detection system is used to detect an image of UV rays with a camera, which is provided with a UV sensor for detecting discharge of UV rays caused by insulation deterioration.

Recently, such a conventional discharge detection system is sometimes used for safety management of power facilities. However, the conventional discharge detection system is inconvenient due to its heavy weight and is required to have grounds or criteria for determining malfunction of the power facilities. Moreover, the conventional discharge detection system is generally imported from foreign countries and restricted in terms of use due to its high price.

SUMMARY OF THE INVENTION

The present invention is conceived to solve the problems as described above, and an aspect of the present invention is to provide a method and apparatus for measuring corona discharge of power facilities, which employs a UV sensor including an optical lens to detect occurrence and location of corona discharge in a power uninterrupted state, when the corona discharge occurs due to degradation or insulation deterioration of the power facilities, so that a safety manager of the power facilities can determine conditions of the power facilities based on the detection results in daily inspection, precise examination and component replacement for operation of the power facilities.

In accordance with an aspect of the present invention, an apparatus for measuring corona discharge of power facilities using a UV sensor with an optical lens includes: a UV sensor array including a plurality of sensors receiving UV rays emitted from an analyzing target of a power facility at a location separated a predetermined distance from the analyzing target; an optical lens unit focusing the UV rays emitted from analyzing target of the power facility to the UV sensor array; a signal detector detecting the UV rays received by the UV sensor array in the form of a pulse voltage waveform signal; a UV image processor processing the detected pulse voltage waveform signal into a UV image on a screen; a real image measurement unit disposed in front of the optical lens unit and photographing a real image of the analyzing target; a real image processor displaying a photographed real image of the analyzing target on the screen; a matching unit combining the photographed real image of the analyzing target with the UV image of the UV image processor; and an image/data output unit detecting a location of corona discharge based on the combined UV image and real image.

The real image measurement unit may be inserted into and coupled to a center of the optical lens unit.

In accordance with another aspect of the present invention, a method for measuring corona discharge of power facilities using a UV sensor with an optical lens includes: focusing UV rays emitted from an analyzing target of a power facility by an optical lens unit at a location separated a predetermined distance from the analyzing target, and receiving the UV rays by a UV sensor array including a plurality of sensors; detecting, by a signal detector, the UV rays received by the UV sensor array in the form of a pulse voltage waveform signal; processing the detected pulse voltage waveform signal into a UV image on a screen by a UV image processor; photographing a real image of the analyzing target by a real image measurement unit while displaying a photographed real image of the analyzing target on the screen by a real image processor;

combining the photographed real image of the analyzing target with the UV image of the UV image processor by a matching unit; and detecting a location of corona discharge based on the combined UV image and real image by an image/data output unit.

BRIEF DESCRIPTION OF THE DRAWINGS

The above and other aspects, features and advantages of the invention will become apparent from the following description given in conjunction with the accompanying drawings, in which.

DETAILED DESCRIPTION OF THE EMBODIMENT

Hereinafter, exemplary embodiments of the present invention will be described in detail with reference to the accompanying drawings.

Figure 2:
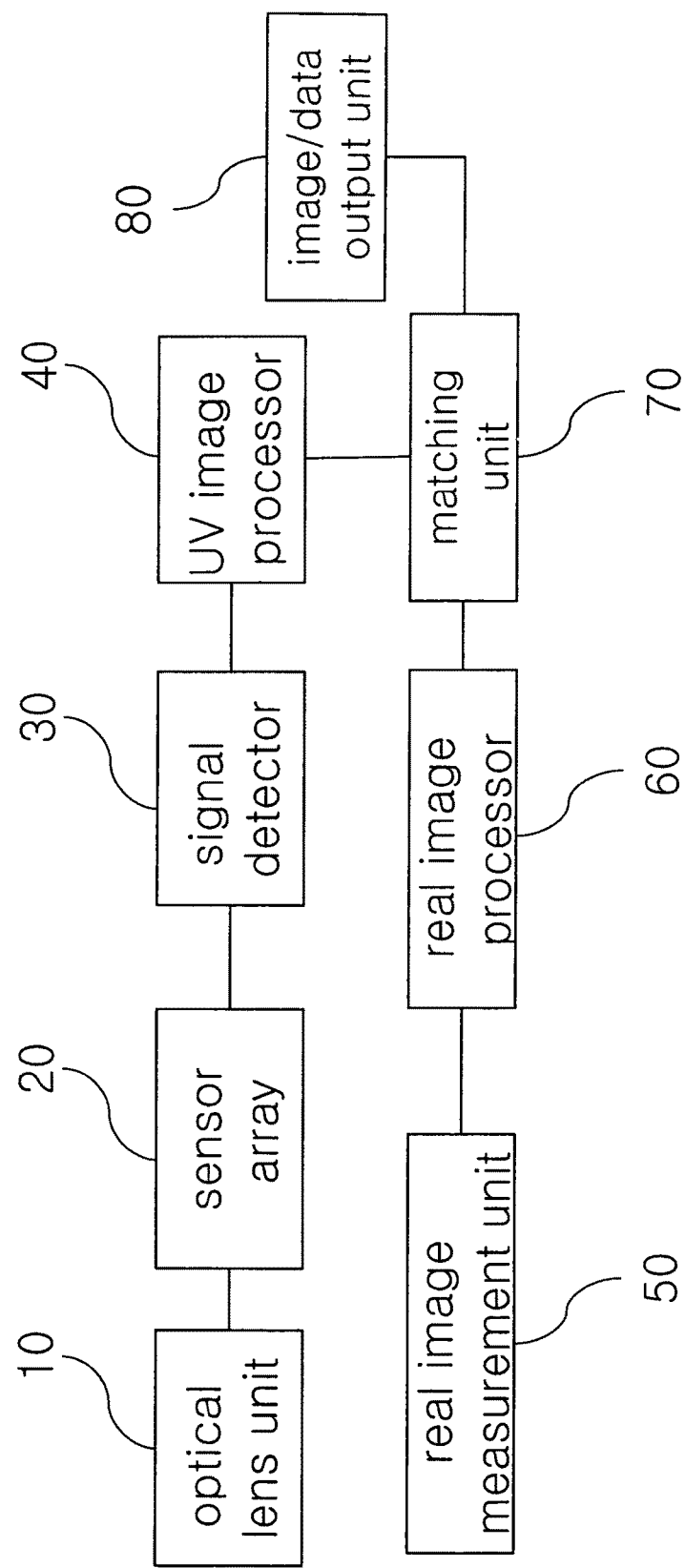
FIG. 2 is a schematic block diagram of an apparatus for measuring corona discharge of power facilities using a UV sensor including an optical lens in accordance with an exemplary embodiment of the present invention.

FIG. 2 is a schematic block diagram of an apparatus for measuring corona discharge of power facilities using a UV sensor including an optical lens in accordance with an exemplary embodiment of the present invention.

Figure 3:
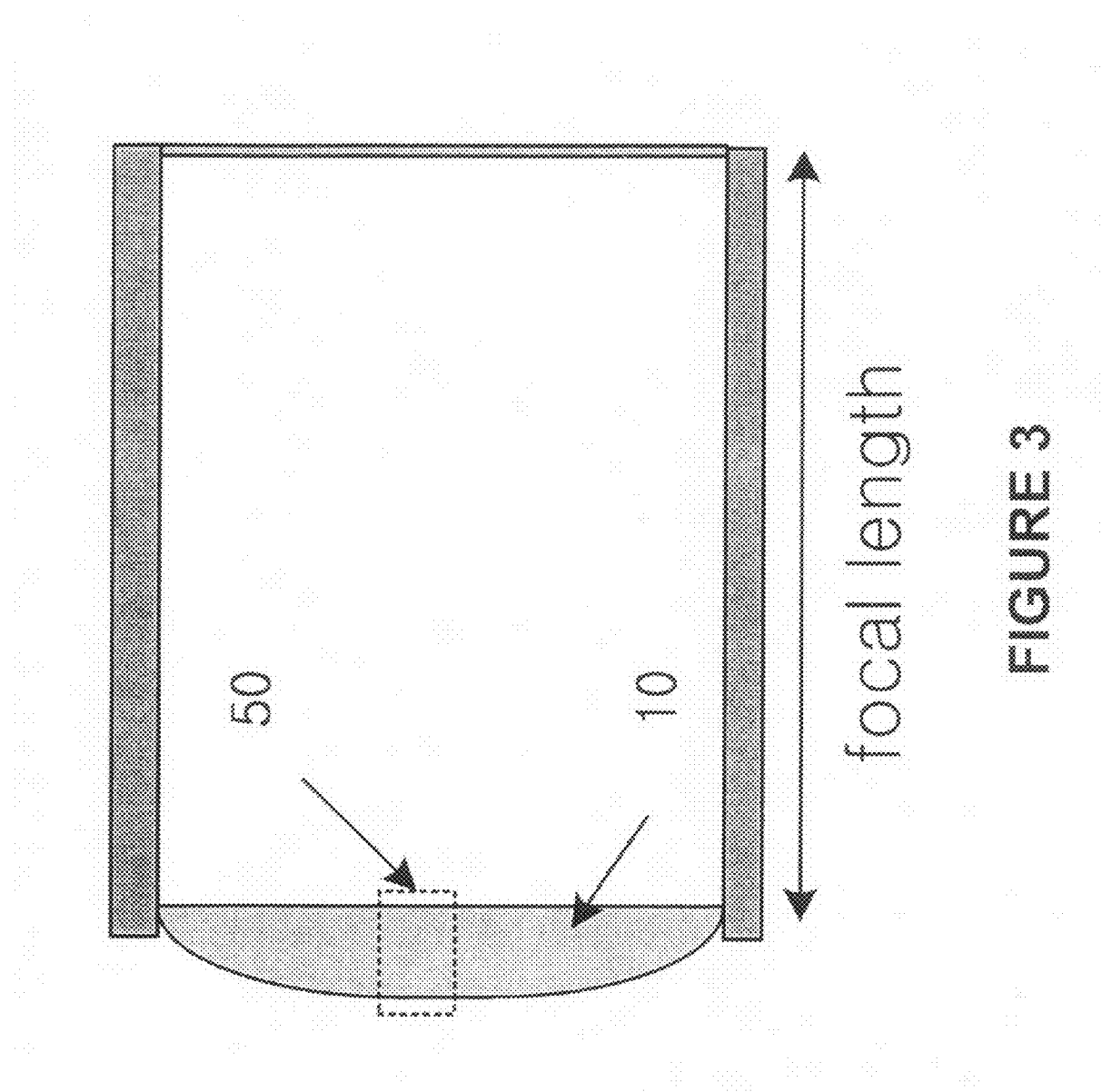
FIG. 3 shows a combined structure of an optical lens unit and a real image measurement unit of the apparatus shown in FIG. 2.

FIG. 3 shows a combined structure of an optical lens unit and a real image measurement unit of the apparatus shown in FIG. 2.

Referring to FIG. 2, an apparatus for measuring corona discharge of power facilities using a UV sensor including an optical lens according to an embodiment is positioned at a location separated a predetermined distance from an analyzing target of a power facility, such as an insulator, cable terminal connector, bushing, and the like to detect UV rays caused by corona discharge of the analyzing target. The apparatus includes an optical lens unit 10 for receiving a UV image, a sensor array 20, a signal detector 30, a UV image processor 40, a real image measurement unit 50 for obtaining a real discharge image of the analyzing target, a real image processor 60, a matching unit 70 for combining the UV image and the real image, and an image/data output unit 80 for outputting the combined UV image and real image.

Referring to FIG. 2, in the apparatus according to the embodiment, the sensor array 20 includes a plurality of UV sensors that are arranged to receive UV rays emitted from the analyzing target of the power facility at a location separated a predetermined distance from the analyzing target.

In FIG. 2, the signal detector 30 detects the UV rays received by the UV sensor array 20 in the form of a pulse voltage waveform signal, and the UV image processor 40 processes the pulse voltage waveform signal of the IN rays into a UV image on a screen.

In FIG. 2, the real image measurement unit 50 photographs a real image of the analyzing target, and the real image processor 60 displays a photographed real image of the analyzing target on a screen. The matching unit 70 combines the photographed real image of the analyzing target and the UV image of the UV image processor, and the image/data output unit 80 detects a location of corona discharge based on the combined UV image and real image.

Referring to FIG. 3, the optical lens unit 10 focuses the UV rays emitted from the target of the power facility to the UV sensor array 20. Here, the real image measurement unit 50 acts as a camera unit for photographing the real image of the analyzing target of the power facility, and is disposed in front of the optical lens unit 10. Alternatively, the real image measurement unit 50 is inserted into and coupled to an opening formed at the center of the optical lens unit 10.

Referring to FIG. 3, the optical lens unit 10 and the real image measurement unit 50 may be disposed inside a certain frame.

The optical lens unit 10 is adapted to collect UV rays emitted upon corona discharge, and is composed of a lens which has good transmittance and low reflectivity.

In FIG. 3, the real image measurement unit 50 is inserted into the center of the optical lens unit 10, and a camera of the real image measurement unit 50 photographs the real image of the analyzing target.

Further, the frame receiving the optical lens unit 10 and the real image measurement unit 50 therein is configured to provide a constant focal length to recognize a location at which the UV rays are emitted.

Figure 4:
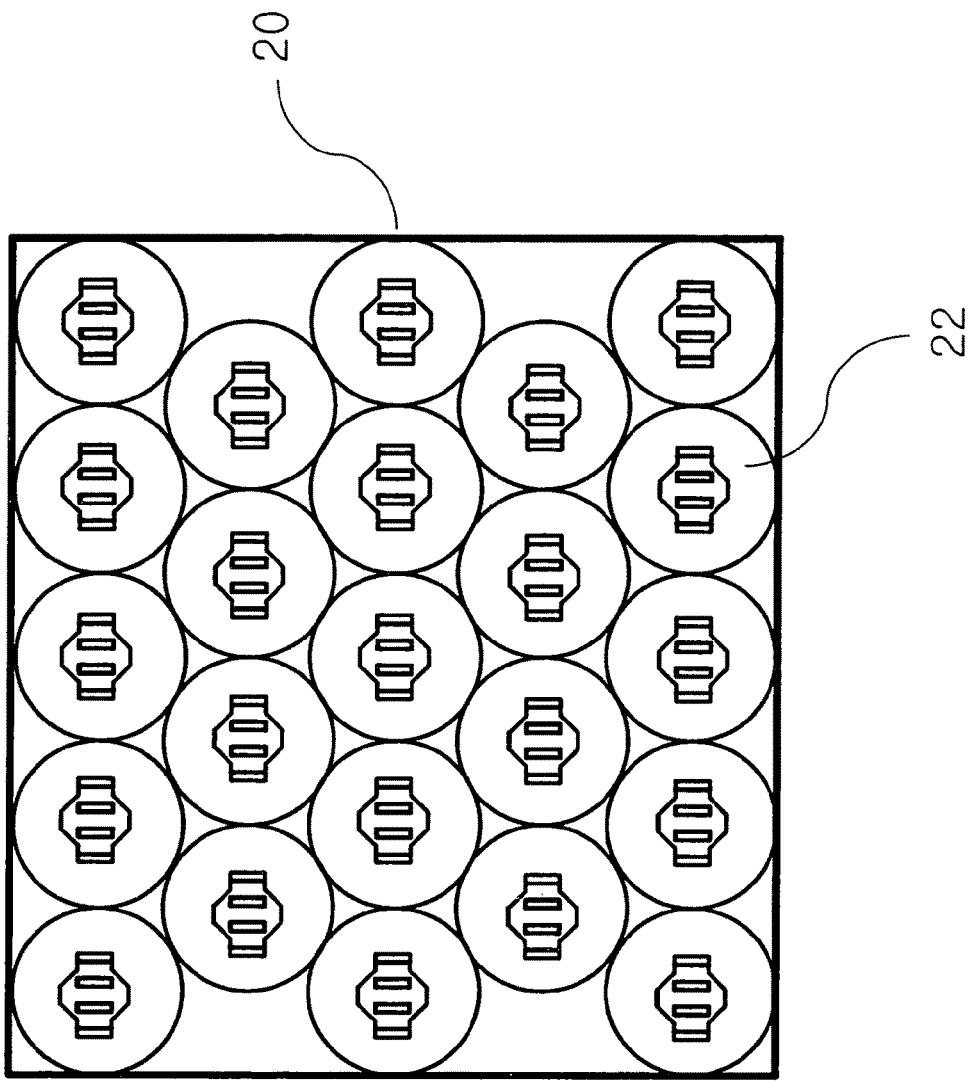
FIG. 4 is a detailed view of a UV sensor array of the apparatus in accordance with the exemplary embodiment of the present invention.

FIG. 4 is a detailed view of the UV sensor array 20 of the apparatus.

Referring to FIG. 4, when photons are discharged upon generation of UV rays resulting from corona discharge, a UV sensor 22 of the UV sensor array 20 detects the UV rays through an anode and cathode of a photo receiver in the UV sensor, and the signal detector 30 detects a pulse voltage waveform signal obtained from the detected UV rays and determines that the UV rays are detected when the peak voltage of the pulse waveform signal is higher than a preset voltage.

The UV sensor array 20 includes a plurality of such UV sensors 22 and is configured to recognize a location of corona discharge from the target of the power facility.

Figure 5:
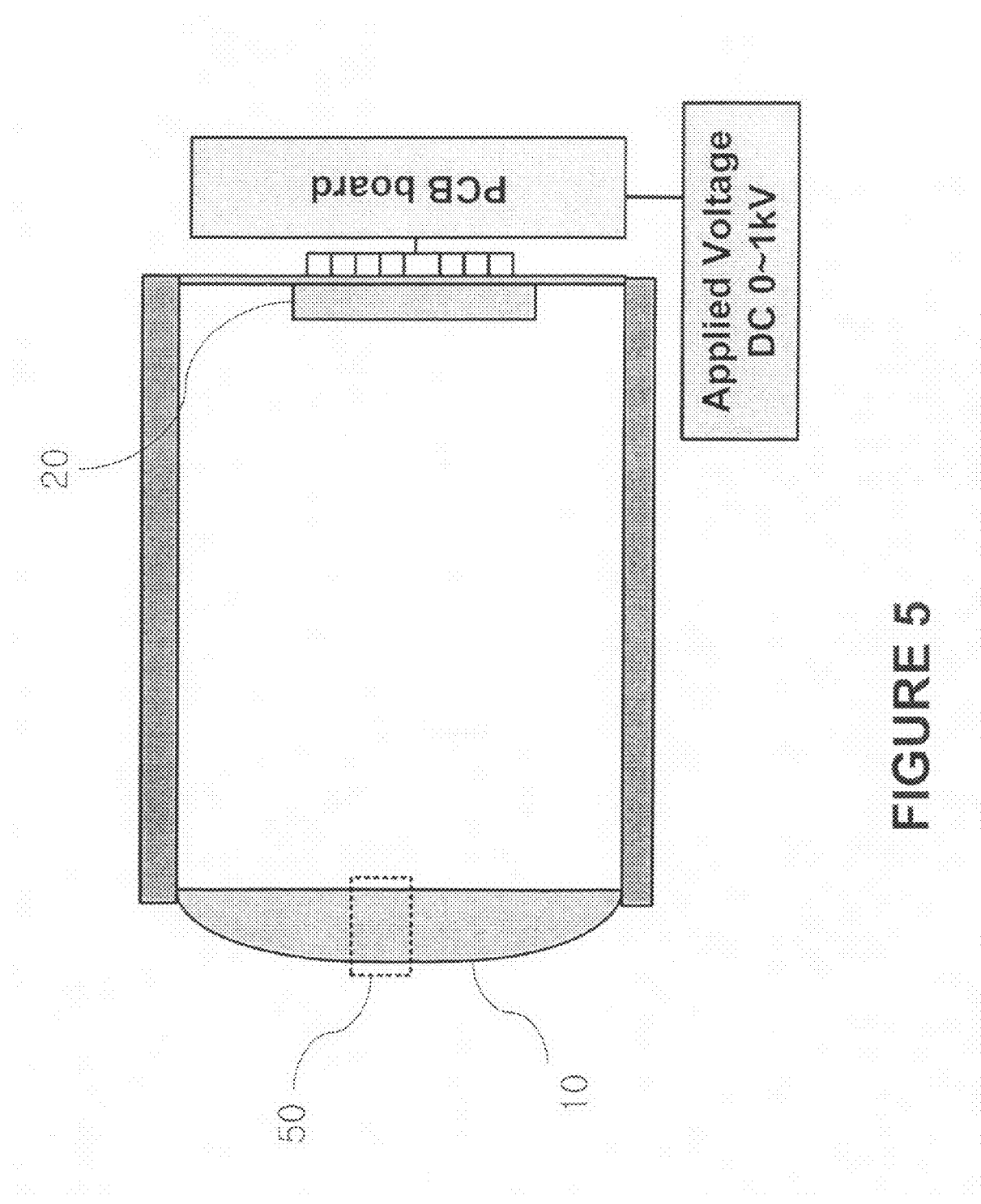
FIG. 5 is a schematic view of the apparatus according to the embodiment, showing the optical lens unit, the real image measurement unit, the UV sensor array, and a UV sensor array driving circuit.

FIG. 5 schematically shows the optical lens unit 10, the real image measurement unit 50, the UV sensor array 20, and a UV sensor array driving circuit.

A DC voltage is supplied to the UV sensor array 20 as shown in FIG. 4 to drive the UV sensors, which in turn detect the photons generated upon corona discharge in the form of a pulse waveform signal.

Here, the DC voltage is 400 V or more and may be varied up to 800 V when detecting the pulse voltage waveform signal.

Figure 6A:
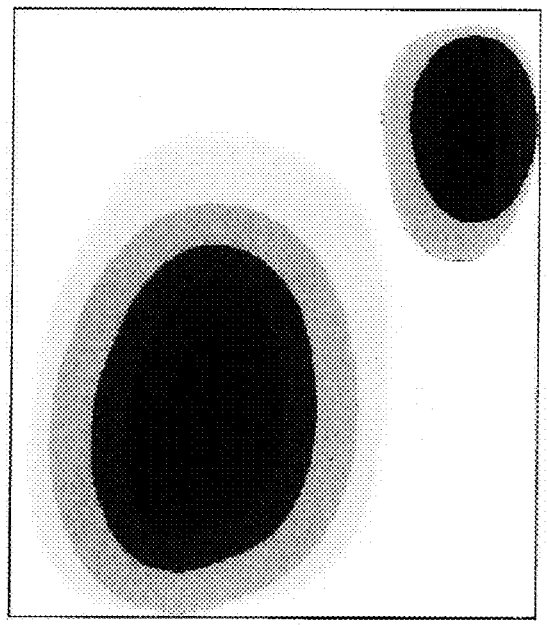
FIGS. 6a and 6b show a process of processing a detected pulse voltage waveform signal into a UV image on a screen by a UV image processor.
Figure 6A:
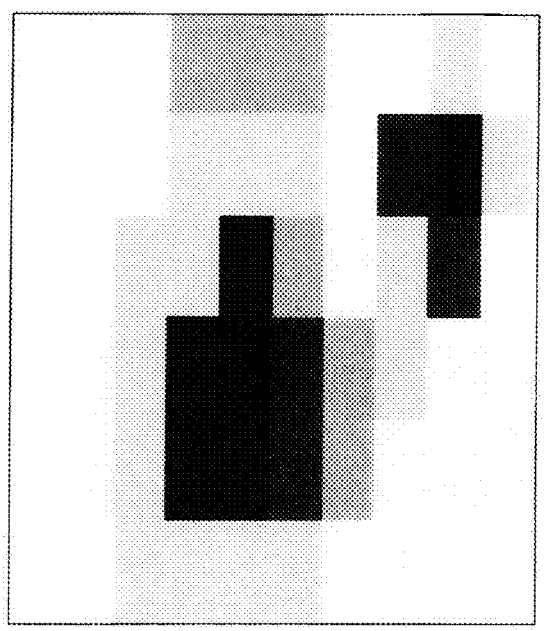
Figure 6B:
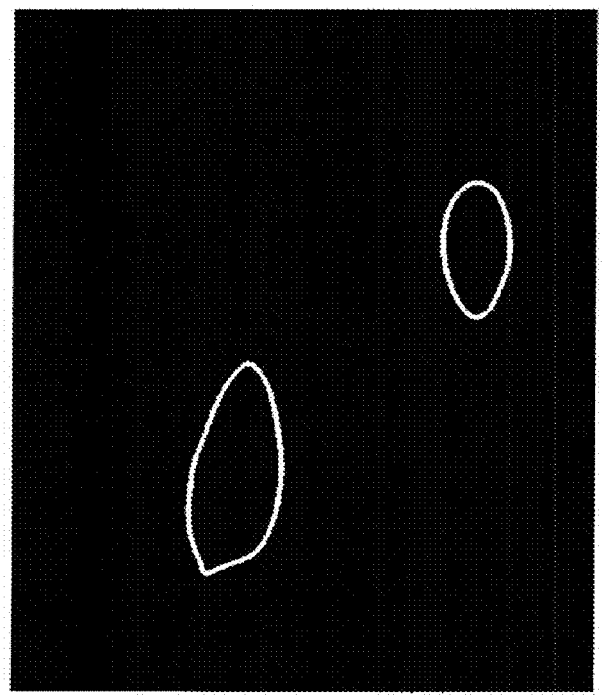
Figure 6B:
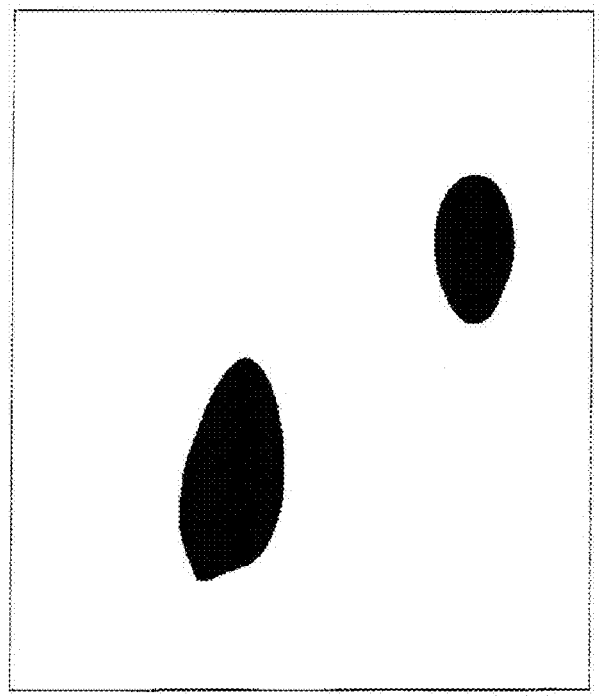

FIGS. 6a and 6b show a process of processing the pulse voltage waveform detected by the signal detector 30 into a UV image on a screen through the UV image processor 40.

In the process, the pulse voltage waveform signal detected by the signal detector 30 is processed to make a resolution of an image signal identical to a resolution of a real image, followed by processing the image signal into a contour line.

Since a UV image has a much lower resolution than the real image as shown in a left side of FIG. 6a when application program is applied to the process, the UV image cannot be directly applied to measurement of corona discharge.

Thus, the UV image may be divided into dark sections and dim sections through interpolation, as shown in a right side of FIG. 6a.

Further, the right-side image of FIG. 6a may be converted into contour lines. The contour lines are formed by a threshold process, in which brightness of a UV image is converted into numerals and a determination is then made for the numerals, with reference to a threshold value, as to whether the numerals are greater than or equal to a threshold value or less than the threshold value to display the contour lines separated at constant intervals from one another. For example, a certain image is displayed as shown in a left side of FIG. 6b through the threshold process, and an outer line is extracted from this image to form a loop image as shown in a right side of FIG. 6b. Then, the UV image may be displayed in the shape of contour lines by overlapping several loop images obtained by repeating this process using various threshold values.

Figure 7:
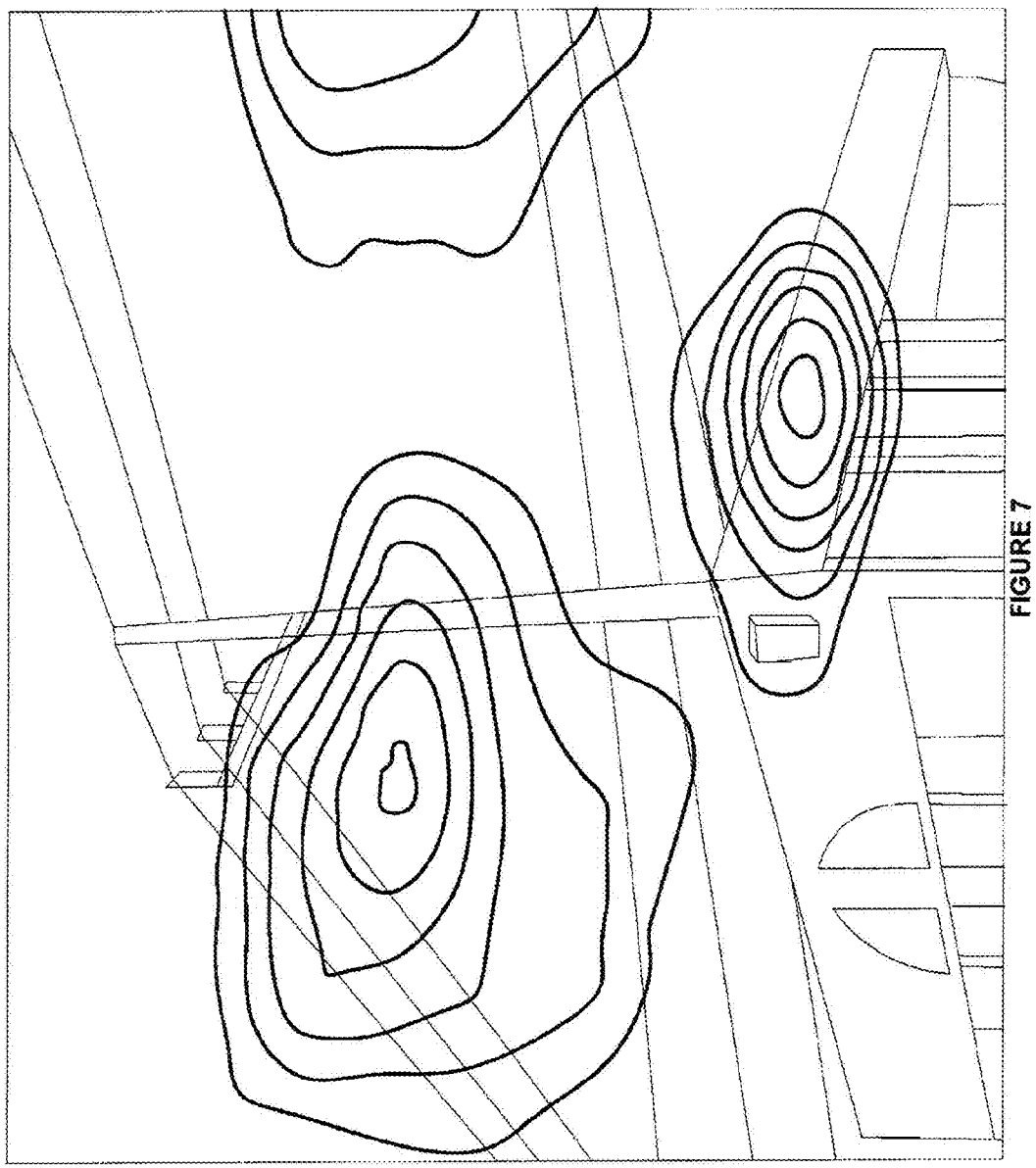
FIG. 7 shows a screen displaying contour lines obtained by combining a real image provided by the real image measurement unit with a UV image provided by the UV image processor of FIGS. 6a and 6b.

FIG. 7 shows a screen displaying contour lines obtained by combining a real image provided by the real image measurement unit with a UV image provided by the UV image processor of FIGS. 6a and 6b, and a UV generation location may be confirmed from this screen.

Figure 1:
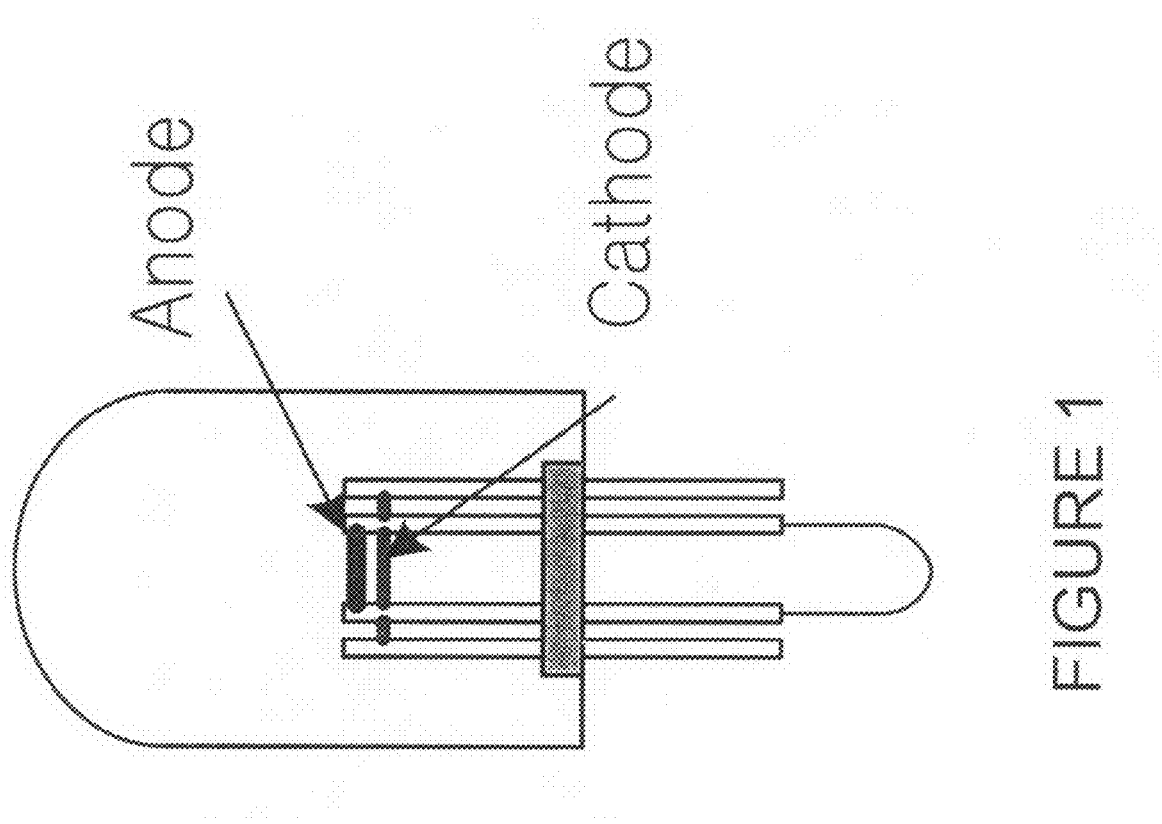
FIG. 1 is a schematic cross-sectional view of a conventional UV sensor.

Next, a process of analyzing corona discharge in the apparatus according to the embodiment will be described with reference to FIG. 1.

First, the optical lens unit 10 focuses UV rays emitted from an analyzing target of a power facility at a location separated a predetermined distance from the analyzing target, and the UV sensor array 30 including a plurality of sensors receives and detects the UV rays.

Then, the signal detector 30 detects the UV rays received by the UV sensor array 20 in the form of a pulse voltage waveform signal.

Next, the UV image processor 40 processes the pulse voltage waveform signal of the UV rays into a UV image on a screen.

Here, the real image measurement unit 50 photographs a real image of the analyzing target, and the real image processor 60 displays a photographed real image of the analyzing target on the screen.

Next, the matching unit 70 combines the photographed real image of the analyzing target and the UV image of the UV image processor.

Finally, the image/data output unit 80 detects a location of corona discharge based on the combined UV image and real image.

As apparent from the above description, according to the embodiment, the apparatus for measuring corona discharge of power facilities using a UV sensor array including an optical lens may detect images and emitting locations of corona discharge UV rays, which are caused by insulation deterioration of power facilities or discharge in air, and may provide the image and discharge data.

Further, the apparatus according to the embodiment enables easy replacement of components due to the use of UV sensors, and can be applied to a portable or on-line monitoring system, which can be used by an expert or an amateur in practice.

Further, the apparatus according to the embodiment may allow a safety manager of power facilities to monitor the power facilities in a power uninterrupted state based on detection information from the apparatus in daily inspection, precise examination, and determination of a replacement cycle for operation of the power facilities.

In understanding the scope of the present invention, terms as used herein are given in consideration of functions of elements of the present invention and can be changed according to intentions or customs of software developers and algorithm analysis in practice. Therefore, the definition of the terms should be made according to the overall disclosure set forth herein.

Although only selected embodiments have been chosen to illustrate the present invention, it will be apparent to those skilled in the art that the embodiments are given by way of illustration only, and that various modifications and changes can be made without departing from the spirit and scope of the present invention as defined by the accompanying claims and their equivalents.

What is claimed is:

1. An apparatus for measuring corona discharge of power facilities using a UV sensor with an optical lens, comprising:
   a UV sensor array including a plurality of sensors receiving UV rays emitted from an analyzing target of a power facility at a location separated a predetermined distance from the analyzing target of the power facility;
   an optical lens unit focusing the UV rays emitted from the analyzing target of a the power facility to the UV sensor array;
   a signal detector detecting the UV rays received by the UV sensor array in the form of a pulse voltage waveform signal;
   a UV image processor processing the detected pulse voltage waveform signal into a UV image on a screen;
   a real image measurement unit disposed in front of the optical lens unit and photographing a real image of the analyzing target of the power facility, wherein the real image measurement unit is inserted into and coupled to a center of the optical lens unit;
   a real image processor displaying the photographed real image of the analyzing target of the power facility on the screen;
   a matching unit combining the photographed real image of the analyzing target of the power facility with the UV image of the UV image processor; and
   an image/data output unit detecting a location of the corona discharge based on the combined UV image and real image.

2. A method for measuring corona discharge of power facilities using a UV sensor with an optical lens, comprising:
   focusing UV rays emitted from an analyzing target of a power facility by an optical lens unit at a location separated a predetermined distance from the analyzing target of the power facility, and receiving the UV rays by a UV sensor array including a plurality of sensors;
   detecting, by a signal detector, the UV rays received by the UV sensor array in the form of a pulse voltage waveform signal;
   processing the detected pulse voltage waveform signal into a UV image on a screen by a UV image processor;
   photographing a real image of the analyzing target of the power facility by a real image measurement unit while displaying a photographed real image of the analyzing target of the power facility on the screen by a real image processor, wherein the real image measurement unit is inserted into and coupled to a center of the optical lens unit;

combining the photographed real image of the analyzing target of the power facility with the UV image of the UV image processor by a matching unit; and detecting a location of the corona discharge based on the combined UV image and real image by an image/data output unit.

* * * * *